United States Patent
Janzig et al.

(10) Patent No.: US 9,950,180 B2
(45) Date of Patent: Apr. 24, 2018

(54) IMPLANTABLE DEVICE WITH CHASSIS ELEMENT

(71) Applicant: MEDTRONIC, INC., Minneapolis, MN (US)

(72) Inventors: Darren A. Janzig, Center City, MN (US); Gerald Lindner, Lino Lakes, MN (US); Chris J. Paidosh, St. Anthony, MN (US); Andrew J. Thom, Maple Grove, MN (US); Brad C. Tischendorf, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 39 days.

(21) Appl. No.: 14/394,507

(22) PCT Filed: Mar. 12, 2013

(86) PCT No.: PCT/US2013/030369
§ 371 (c)(1),
(2) Date: Oct. 15, 2014

(87) PCT Pub. No.: WO2013/162726
PCT Pub. Date: Oct. 31, 2013

(65) Prior Publication Data
US 2015/0094789 A1   Apr. 2, 2015

Related U.S. Application Data

(60) Provisional application No. 61/639,458, filed on Apr. 27, 2012.

(51) Int. Cl.
*A61N 1/375*   (2006.01)

(52) U.S. Cl.
CPC .......... *A61N 1/3758* (2013.01); *A61N 1/375* (2013.01); *A61N 1/3752* (2013.01)

(58) Field of Classification Search
CPC ........................... A61N 1/3752; A61N 1/3758
See application file for complete search history.

(56) References Cited

U.S. PATENT DOCUMENTS

| 6,327,502 B1 * | 12/2001 | Johansson | .............. A61N 1/375 607/36 |
|---|---|---|---|
| 2003/0204207 A1 | 10/2003 | MacDonald | |

(Continued)

FOREIGN PATENT DOCUMENTS

WO   WO 2008/088568   7/2008

OTHER PUBLICATIONS

PCT International Preliminary Report on Patentability for International Application No. PCT/US2013/030369 dated Nov. 6, 2014 (6 pages).

(Continued)

*Primary Examiner* — Tammie K Heller
(74) *Attorney, Agent, or Firm* — Mueting, Raasch & Gebhardt, P.A.

(57) ABSTRACT

A implantable active medical device includes a chassis plate having a first major surface and an opposing second major surface, an elongate lead connector fixed to the first major surface and extending orthogonally away from the first major surface and a circuit board fixed to the first major surface and extending orthogonally away from the first major surface. A hermetic housing defines a sealed housing cavity. The hermetic housing is fixed to the first major surface. The elongate lead connector and the circuit board are disposed within the sealed housing cavity.

24 Claims, 8 Drawing Sheets

(56) References Cited

U.S. PATENT DOCUMENTS

2006/0089682 A1 4/2006 Kronich
2009/0034769 A1* 2/2009 Darley ............... A61N 1/36032
                                                                381/328

OTHER PUBLICATIONS

PCT International Search Report and Written Opinion for International Application No. PCT/US2013/030369 dated Sep. 17, 2013 (8 pages).

* cited by examiner

IMPLANTABLE DEVICE WITH CHASSIS ELEMENT

This application is a U.S. National Stage Application of International Application No. PCT/US2013/030369, filed Mar. 12, 2013, which was published in English on Oct. 31, 2013, International Patent Publication WO 2013/162726 A1, which claims the benefit under 35 U.S.C. 119(e) of U.S. Provisional Application No. 61/639,458, filed Apr. 27, 2012.

BACKGROUND

Implantable active medical devices, such as cardiac rhythm management devices (pacemakers and defibrillators) and a variety of implantable muscle/nerve stimulators, for example, generally include a battery and battery-powered electronic pulse generator contained within a hermetically sealed housing or case and attached to a lead connector housing or block. The lead connector block is often affixed to the hermetically sealed housing with brackets, metal solder, and/or a medical grade adhesive. The connector housing contains components that electrically connects a therapy lead to the pulse generator electronics.

The electronics within the hermetically sealed housing are conductively coupled to the lead connector block with an electrical feedthrough assembly. Electrical feedthroughs serve the purpose of providing a conductive path extending between the interior of a hermetically sealed container and a point outside the hermetically sealed housing. The conductive path through the feedthrough usually includes a conductor pin or terminal that is electrically insulated from the hermetically sealed housing. While this arrangement has proven to be highly reliable, it involves a variety of expensive manufacturing processes and parts that necessarily increase the cost and overall volume of the resulting product.

In many implantable active medical devices in industry, the device housing (also known as shields) provide the structure to which internal components are fixed. Most often the shields are made of thin metallic material and therefore the major surfaces can be somewhat flexible. Components may be fixed to the flexible surfaces by means such as epoxy or pressure sensitive adhesive resulting in relative movement between the internal components. Strain relief for electrical or mechanical interconnects between components is required to improve device lifetime.

Ongoing efforts by the industry to reduce the size of the implantable device are desired. Early implantable pacemakers back in the 1960's were about the size of a hockey puck. With advances in microelectronics and integrated circuitry, significantly more features and capabilities have been embodied in implantable active medical devices that can be very small. Nonetheless, efforts to further reduce the size of implantable active medical devices continue in the industry.

BRIEF SUMMARY

The present disclosure relates to an implantable medical device having a chassis element. In particular the present disclosure relates to an implantable medical device having a chassis element with an elongate lead connector and circuit board fixed to and extending orthogonally away from the chassis element. The chassis element may also provide rigid fixation for additional components such as a battery or communication/recharge coil.

In one illustrative embodiment, an implantable active medical device includes a chassis plate having a first major surface and an opposing second major surface, an elongate lead connector fixed to the first major surface and extending orthogonally away from the first major surface and a circuit board fixed to the first major surface and extending orthogonally away from the first major surface. A hermetic housing defines a sealed housing cavity. The hermetic housing is fixed to the first major surface. The elongate lead connector and the circuit board are disposed within the sealed housing cavity.

In another illustrative embodiment, an implantable active medical device includes a chassis plate having a first major surface and an opposing second major surface, a first elongate lead connector is fixed to the first major surface and extends orthogonally away from the first major surface and a second elongate lead connector is fixed to the first major surface and extends orthogonally away from the first major surface. A circuit board is fixed to the first major surface and extends orthogonally away from the first major surface and is disposed between the first elongate lead connector and the second elongate lead connector. A hermetic housing defines a sealed housing cavity and is fixed to the first major surface. The first elongate lead connector, second elongate lead connector and the circuit board are disposed within the sealed housing cavity.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
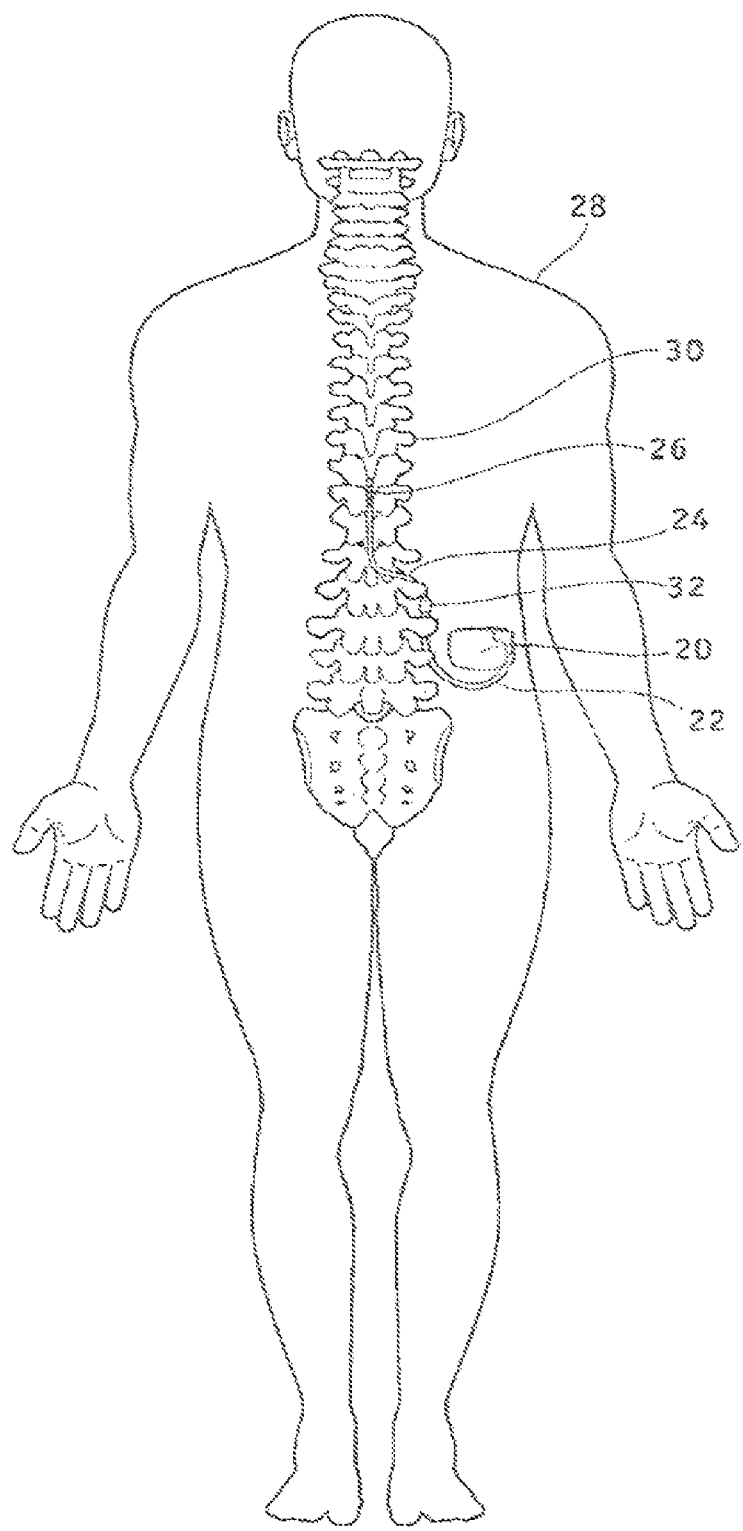
FIG. 1 is a schematic diagram of a an active medical device implanted within a human body.

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if an element depicted in the figures is turned over or flipped over, portions previously described as below or beneath other elements would then be above those other elements.

As used herein, when an element, component or layer for example is described as being "on" "connected to", "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as begin "directly on", "directly connected to", "directly coupled with", or "directly in contact with" another element, there are no intervening elements, components or layers for example.

The present disclosure relates to an implantable medical device having a chassis element. In particular the present disclosure relates to an implantable medical device having a chassis element with an elongate lead connector and circuit board fixed to and extending orthogonally away from the chassis element. In some embodiments there are at two elongate lead connectors fixed to and extending orthogonally away from the chassis element. The circuit board can be disposed between the lead connectors. The chassis element provides a rigid support structure that maintains the displacement between components fixed to the chassis element, minimizing the amount of strain relief needed between those components. Components can be but not limited to a circuit board, battery, lead connectors, and communication/recharge coils. The chassis element also enables the use of multiple or different battery options based on the specific therapy indication. The chassis element also provides access to at least two sides of the functional elements within the device. While the present disclosure is not so limited, an appreciation of various aspects of the disclosure will be gained through a discussion of the examples provided below.

FIG. 1 is a schematic diagram of an active medical device 20 implanted within a human body or patient 28. The implanted active medical device 20 is illustrated as a neurostimulator, however, the implanted active medical device 20 can be any "active implantable medical device" or "implantable signal generator" as described above and can be placed in any location within a body cavity or tissue within the body, or on the surface of a patient's skin, as desired.

The active medical device 20 is coupled to a lead extension 22 having a proximal end coupled to the active medical device 20, and a lead 24 having a proximal end coupled to a distal end 32 of the lead extension 22 and a distal end of the lead 24 coupled to one or more electrodes 26. In other embodiments, the lead 24 proximal end is coupled to the active medical device 20, without a need for a lead extension 22. The active medical device 20 can be implanted in any useful region of the body such as in the abdomen of a patient 28, and the lead 24 is shown placed somewhere along the spinal cord 30. In some embodiments, the active medical device 20 has one or two leads each having four to eight electrodes or more electrodes. Such a system may also include a physician programmer and a patient programmer (not shown). The active medical device 20 can be considered to be an implantable signal generator of the type available from Medtronic, Inc. and capable of generating multiple signals occurring either simultaneously or one signal shifting in time with respect to the other, and having independently varying amplitudes and signal widths. The active medical device 20 contains a power source and the electronics for sending precise, electrical signals to the patent to provide the desired treatment therapy. While the active medical device 20, in many embodiments, provides electrical stimulation by way of signals, other forms of stimulation may be used as continuous electrical stimulation.

In many embodiments, the lead 24 is a wire having insulation thereon and includes one or more insulated electrical conductors each coupled at their proximal end to a connector and to contacts/electrodes 26 at its distal end. Some leads are designed to be inserted into a patient percutaneously (e.g. the Model 3487A Pisces—Quad® lead available from Medtronic, Inc.), and some are designed to be surgically implanted (e.g. Model 3998 Specify® lead, also available form Medtronic, Inc.). In some embodiments, the lead 24 may contain a paddle at its distant end for housing electrodes 26. In many embodiments, electrodes 26 may include one or more ring contacts at the distal end of lead 24.

Figure 2:
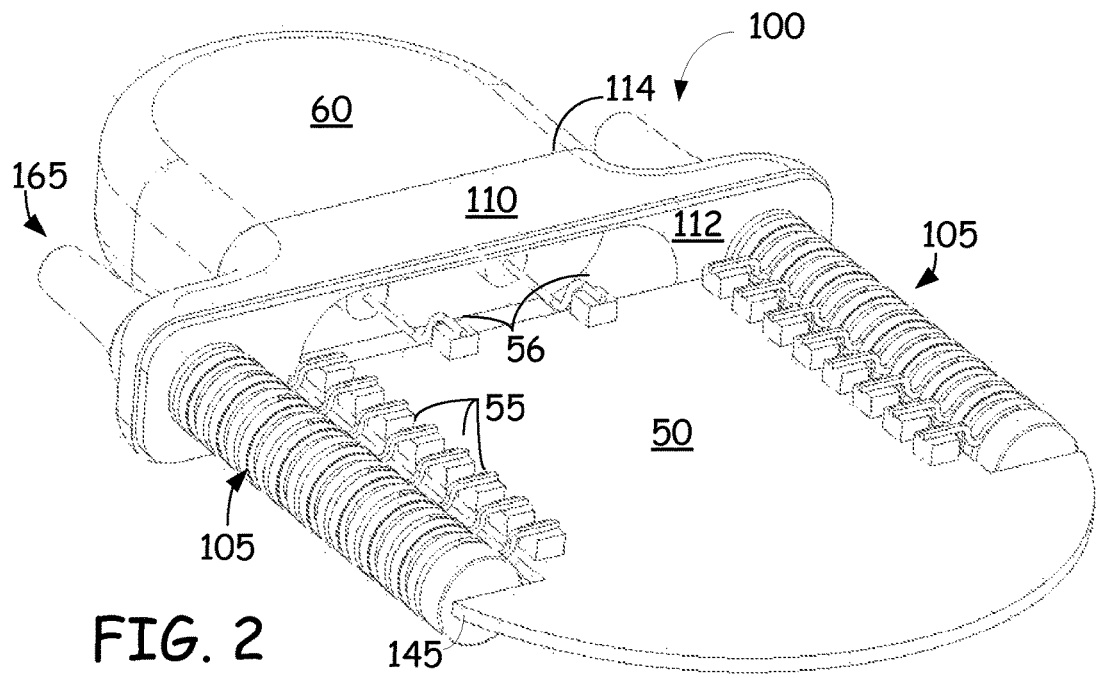
FIG. 2 is a schematic perspective view of an implantable active medical device with an internal hermetic lead connector with hermetic housing removed for illustration.
Figure 3:
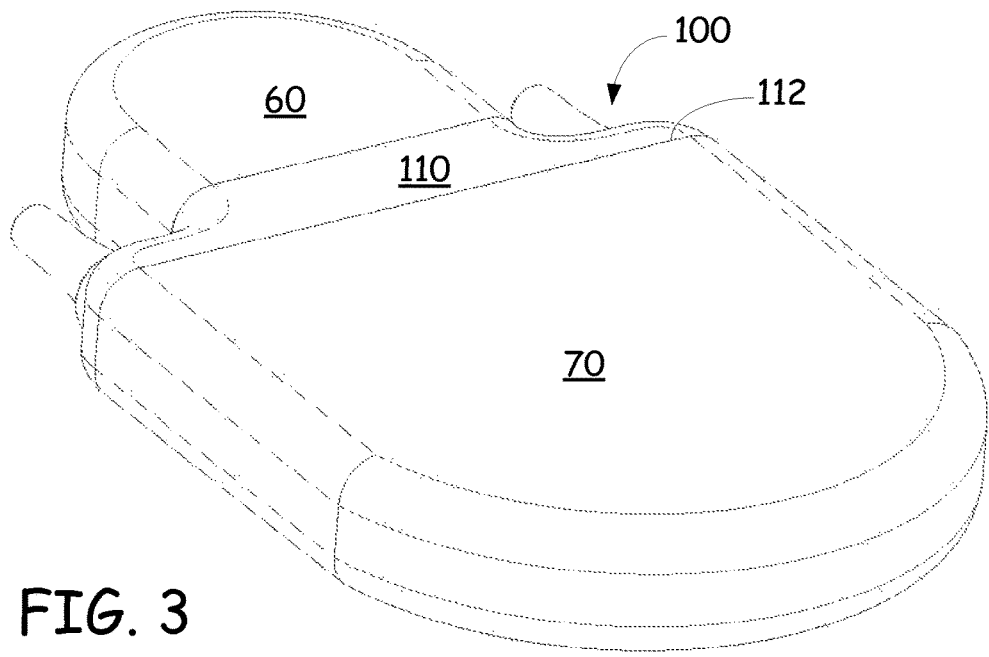
FIG. 3 is a schematic perspective view of the implantable active medical device of FIG. 2 with a hermetic housing in place.

FIG. 2 is a schematic perspective view of an implantable active medical device 100 with the hermetic housing removed for illustration. FIG. 3 is a schematic perspective view of the implantable active medical device 100 of FIG. 2 with the hermetic housing 70 in place.

In many embodiments, an implantable active medical device includes a chassis plate 110 having a first major surface 112 and an opposing second major surface 114. In many embodiments, the chassis plate 110 has a substantially planar first major surface 112 and/or a substantially planar opposing second major surface 114. In many of these embodiments, the substantially planar first major surface 112 and substantially planar opposing second major surface 114 are parallel with each other. In some embodiments the chassis plate 110 has a substantially non-planar first major surface 112 and/or a substantially non-planar opposing second major surface 114. Functional elements of the implantable active medical device are fixed to the chassis plate to maintain displacement between functional elements. The chassis element or plate 110 can be formed of a metal or other rigid structural material. In many embodiments the chassis element or plate 110 can be formed of titanium or a titanium alloy. In many embodiments, the thickness (distance between the first major surface 112 and an opposing second major surface 114) is in a range of about 1 to 10 mm or from about 4 to 8 mm.

At least one elongate lead connector 105 is fixed to the first major surface 112 and extends away from the first major surface 112. In many embodiments at least one elongate lead connector 105 is fixed to the first major surface 112 and extends orthogonally away from the first major surface 112. In some embodiments, at least one elongate lead connector 105 is fixed to the first major surface 112 and extends at any angle away from the first major surface 112. In many embodiments the elongate lead connector 105 is welded to the second major surface 114 and/or first major surface 112 and/or extends through the thickness of the chassis element or plate 110.

FIG. 2 illustrates an implantable active medical device 100 having two elongate lead connectors 105. In other embodiments the implantable active medical device 100 has three or four or more elongate lead connectors 105. The illustrated lead connector 105 is an elongate member extending between a lead aperture 165 first open end and an end cap 145, and having an inner surface defining an open lumen lead aperture 165. The elongate lead connector 105 is further described with regard to FIGS. 4-8 below.

Electronics 50 are fixed to the first major surface 112 and extending orthogonally away from the first major surface 112. Electronics can be any useful electronics such as a circuit board. A circuit board can include both a printed circuit board (often a rigid printed circuit board) and a flexible circuit (also known as a flex circuit), or a combination of a printed circuit board and a flex circuit. In many embodiments the elongate lead connectors 105 are fixed at only one end (proximal end) to the first major surface 112 of the chassis plate 110 and is not fixed at an opposing distal end. In these embodiments, the elongate lead connectors 105 is in cantilever arrangement within the hermetic enclosure of the hermetic housing 70.

In many embodiments, the electronics 50 include a hybrid or circuit board fixed to the first major surface 112 and extending orthogonally away from the first major surface 112. In many embodiments the elongate lead connector 105 is coextensive with the circuit board 50. In many embodiments the elongate lead connector 105 is fixed to the circuit board 50. In some embodiments the elongate lead connector 105 is fixed to the circuit board 50 via direct electrical connections 55 between the elongate lead connector 105 and the circuit board 50 as illustrated in FIG. 2. The electronics 50 generally control the active medical device. In some embodiments, the electronics 50 includes memory. The memory can be any magnetic, electronic, or optical media, such as random access memory (RAM), read-only memory (ROM), electronically-erasable programmable ROM, flash memory, or the like. The functional elements can be independently fixed to the first major surface 112 or the opposing second major surface 114 in any arrangement.

A hermetic housing 70 defines a sealed housing cavity. The hermetic housing 70 is fixed to the first major surface 112. The elongate lead connector 105 and the circuit board 50 are disposed within the sealed housing cavity. In many embodiments the hermetic housing 70 is a metallic shell.

In many embodiments, as illustrated, a power source 60 is fixed to the chassis 110 second major surface 114. In other embodiments the power source 60 is fixed to the chassis 110 first major surface 112. The power source 60 can include a battery, for example disposed within a hermatic shield or shell. The battery 60 can form a portion of the exterior surface of the implantable active medical device. In some embodiments the chassis 110 enables the use of a number of different batteries having different sizes or capacities or configurations as required by different therapy indications. The power source 60 can be electrically connected to the circuit board 50 through the chassis plate 110 via electrical connectors 56. The power source 60 can be any useful battery or inductive coil.

Figure 4:
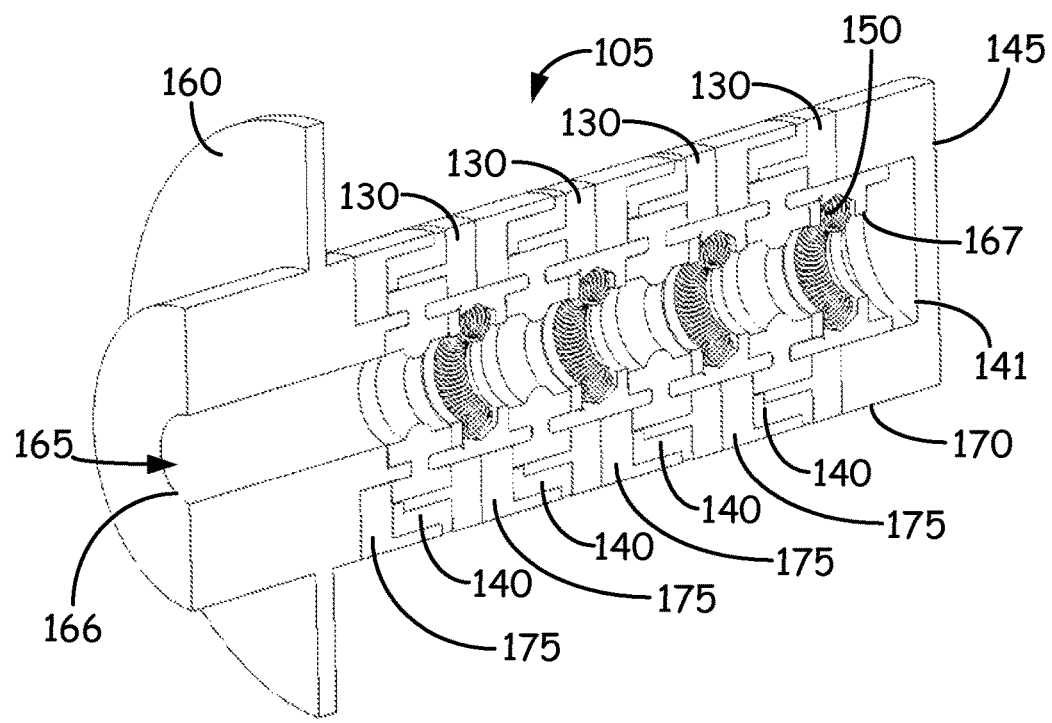
FIG. 4 is a perspective cross-sectional view of an illustrative lead connector.
Figure 5:
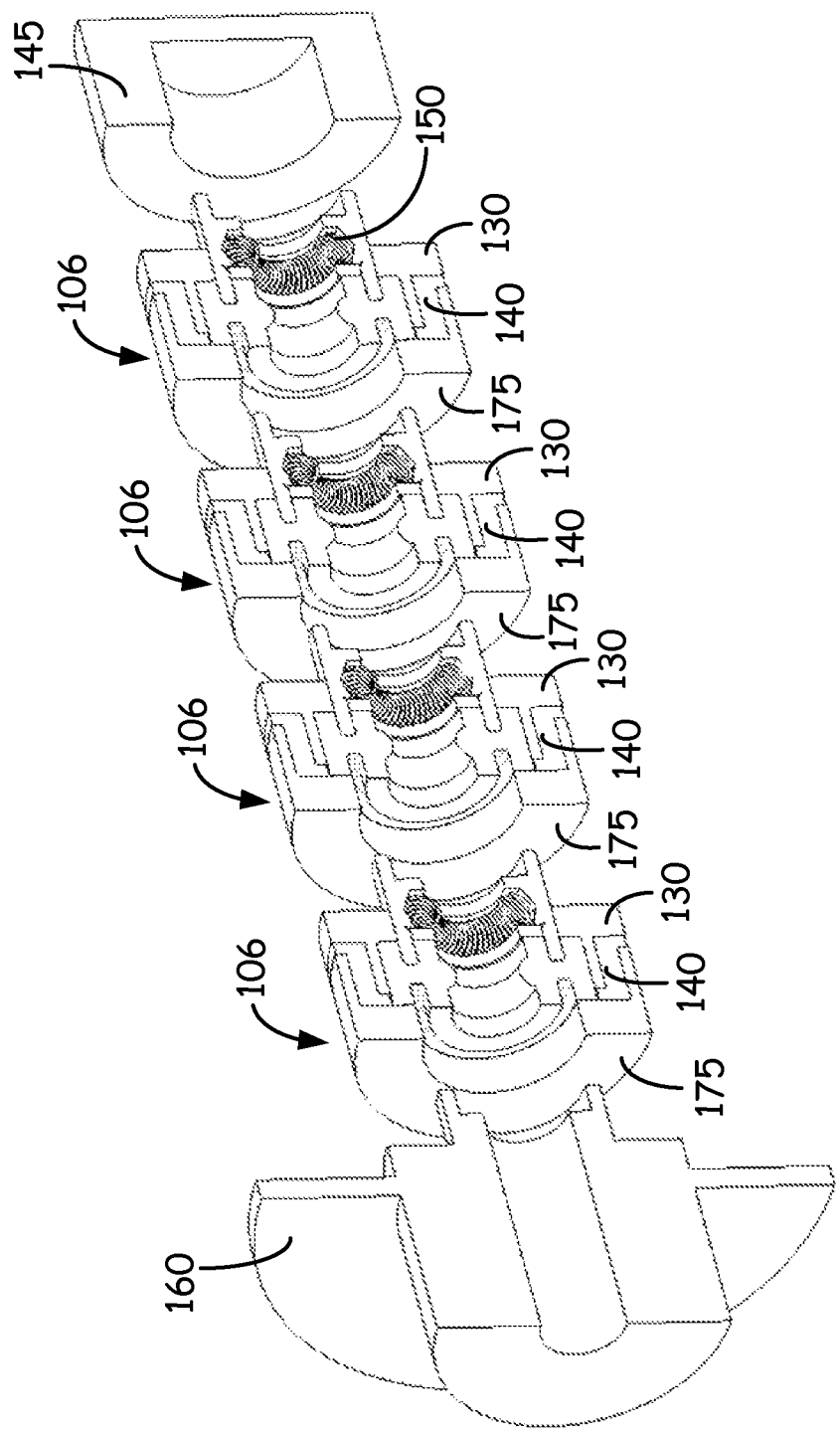
FIG. 5 is an exploded perspective cross-sectional view of the illustrative lead connector shown in FIG. 4.
Figure 6:
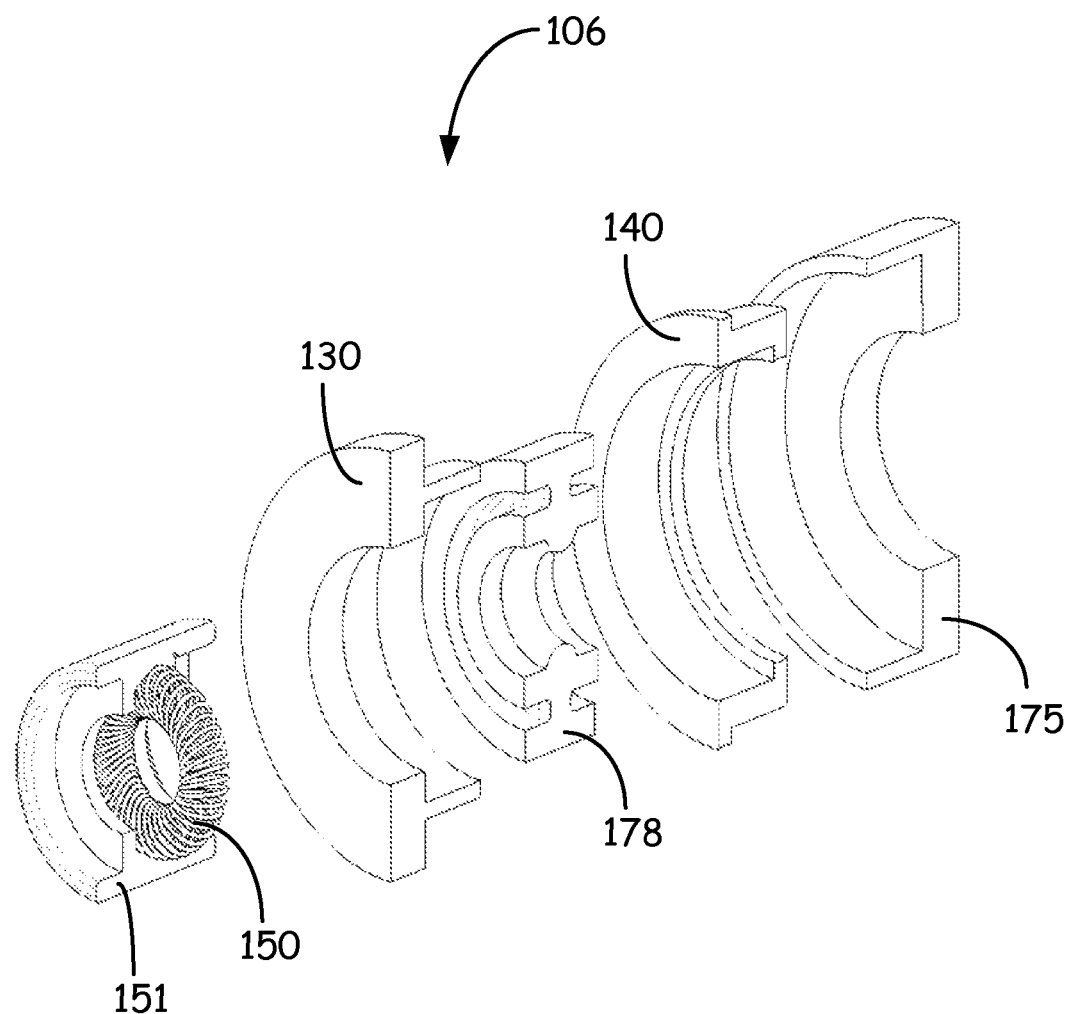
FIG. 6 is an exploded perspective cross-sectional view of one of the illustrative lead connector sub-assemblies shown in FIG. 5.
Figure 7:
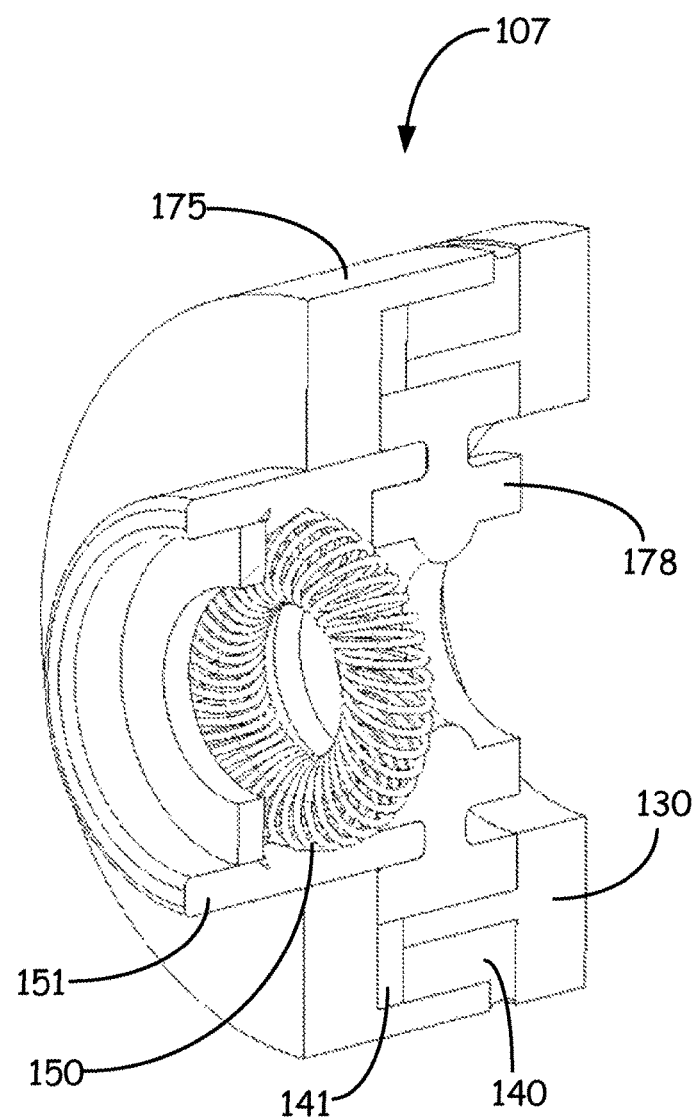
FIG. 7 is a perspective cross-sectional view of another illustrative lead connector sub-assembly.
Figure 8:
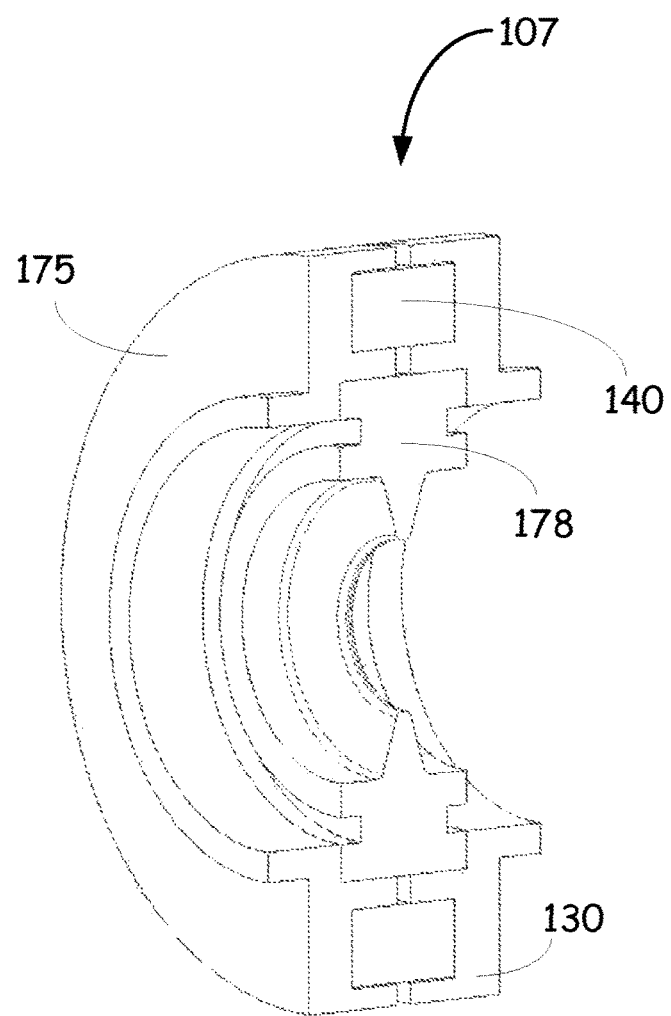
FIG. 8 is a perspective cross-sectional view of another illustrative lead connector sub-assembly.

The elongate lead connector 105 defines at least a portion of the hermetic barrier. The lead connector 105 can be utilized to provide the hermetic barrier extending into a device. FIG. 4 is a perspective cross-sectional view of an illustrative elongate lead connector 105. FIG. 5 is an exploded perspective view of the illustrative elongate lead connector 105 shown in FIG. 4. FIG. 6 is an exploded perspective view of one of the illustrative elongate lead connector sub-assemblies 106 shown in FIG. 5. FIG. 7 is a perspective view of another illustrative elongate lead connector sub-assembly 107. FIG. 8 is a perspective cross-sectional view of another illustrative lead connector sub-assembly 107.

The lead connector 105 includes one or more subassemblies that include of two electrically conducting contact rings 130 and 175 spaced apart by electrically insulating material 140. Multiple subassemblies may be joined together such as laser welding to form a hermetic tube, by welding adjacent electrically conducting contact rings together. The two or more electrically conducting contact rings 130, 175 provide electrical communication between the electronics or circuit board 50 and the lead contact 150, 151. The lead connector 105 provides a hermetic seal between the sealed housing 70 interior and the lead aperture 165.

The electrically conducting contact rings can be formed of any useful electrically conductive material and also form a hermetic bond. In many embodiments, the electrically conducting contact rings are formed of a metallic material such as, for example, titanium, stainless steel, MP35N, niobium, tantalum, platinum, and alloys or combinations thereof. In some embodiments, the electrically conducting contact rings are formed of a metallic material such as, for example, titanium.

The electrically insulating material 140 can be formed of any useful electrically insulating material. In many embodiments the electrically insulating material 140 is a ceramic or glass material. Glass for formation of electrical insulating member 140 includes boro-alumino, boro-alumino silicate and/or boro silicate type glasses. The element(s) and/or compounds used to form electrical insulating member 140 are selected in a manner to reduce tensile stresses with conducting contact rings 130. For example, electrical insulating member 140, employing glass, has a coefficient of thermal expansion (CTE) value about equivalent to or within 15% of the CTE associated with conducting contact rings 130.

Figure 9:
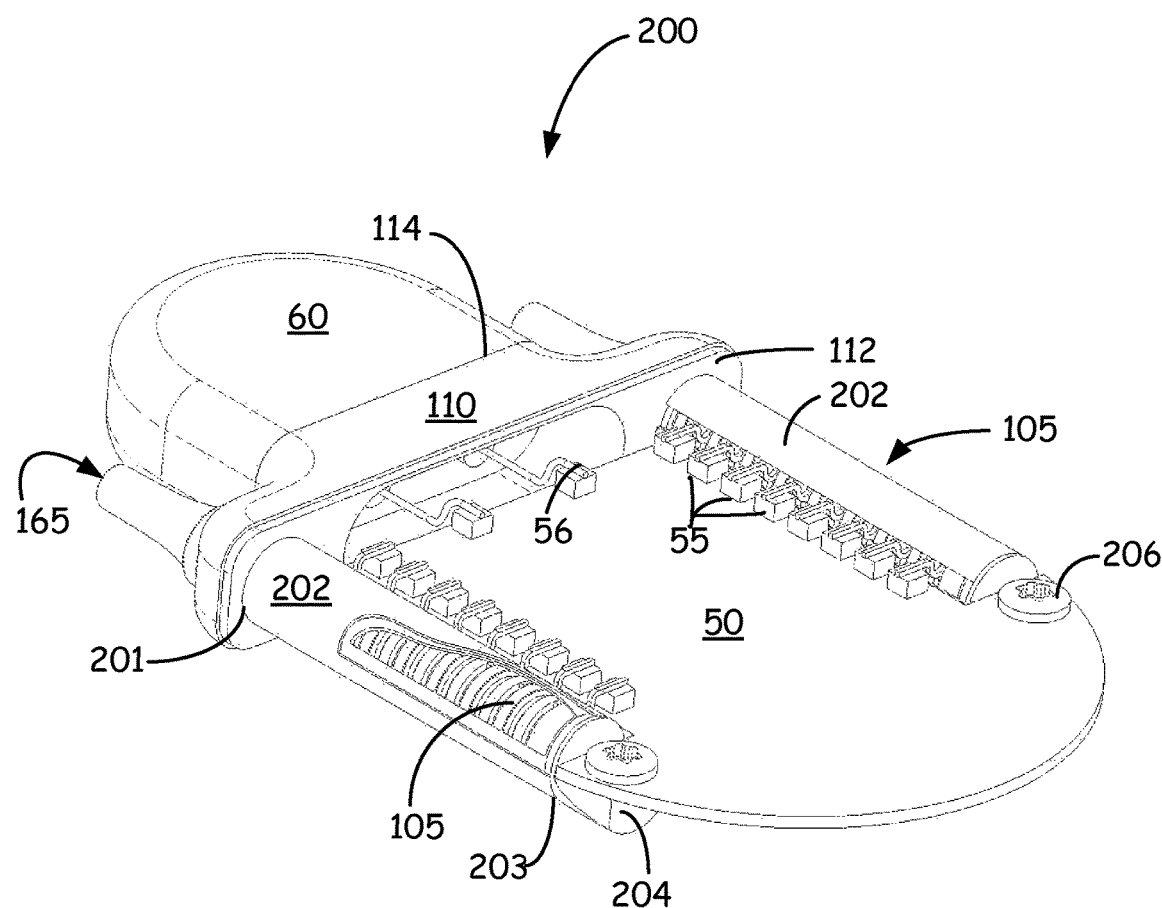
FIG. 9 is a schematic perspective view of another implantable active medical device with an internal hermetic lead connector with hermetic housing removed for illustration.

In some embodiments, a filtering capacitor is disposed between the electrically conducting contact rings 130, 175 and the electronics 50 (as illustrated in FIG. 9). The filtering capacitor can effectively filter out undesirable electromagnetic interference (EMI) from the active medical device 102.

Placement of the lead connector 105 within the hermetically sealed active medical device housing enables a direct electrical connection between the lead connector 105 and the electronics 50. In addition, the elimination of a traditional feedthrough can reduce the size and volume of the implantable active medical device and can also reduce the number of parts and connections needed to assemble the implantable active medical device. The chassis plate provides rigid support structure that maintains/minimizes the displacement between components fixed to the chassis element and provides access to at least two sides of the functional elements within the device.

The illustrated lead connector 105 is an elongate member extending between a lead aperture 165 first open end 166 and end cap 145, and having an inner surface 167 defining an open lumen lead aperture 165. The open lumen lead aperture 165 or lead receptacle 165 is configured to accept one lead or lead extension, as described above, and electrically couple one or more lead contacts with one or more connector contacts 150 nested in the elongate body of the lead connector 105, that in many embodiments is generally cylindrical. FIG. 8 lead connector sub-assembly 107 is illustrated without a separate contact element (element 150 is other figures) but it is understood that it could include a contact element as illustrated in FIG. 7.

In many embodiments, the lead aperture 165 is a cylindrical open lumen of generally circular cross-sectional area formed by an inner surface of the electrically conducting rings 130, 175 and electrically insulating rings 140 bonded together in axial alignment. The lead connector 105 defines a lead connector outer surface 170 and at least a portion of the lead connector outer surface 170 is disposed within the sealed housing 70 interior. In many embodiments, at least a majority of the lead connector outer surface 170 is disposed within the sealed housing 70 interior. In many embodiments, substantially the entire lead connector outer surface 170 is disposed within the sealed housing 70 interior and at least partially defines the sealed housing 70 interior. In some embodiments, the entire lead connector outer surface 170 is disposed within the sealed housing 70 interior.

In the illustrated embodiment, the lead connector 105 is formed of one or more electrically conducting contact rings 130, 175 spaced apart by electrically insulating rings 140. The one or more electrically conducting contact rings 130, 175 are in electrical communication with the electronics (described above), and the lead connector 105 body provides a hermetic seal between the sealed housing interior/lead connector outer surface 170 and the lead aperture 165. The one or more electrically conducting contact rings 130, 175 and electrically insulating rings 140 are assembled in axial alignment to form the lead connector 105. The electrically insulating rings 140 can provide structural integrity and/or a hermetic bond between 130 and 175. Adjacent 130 and 175 rings are then joined typically by laser welding The one or more electrically conducting contact rings 130, 175 can include one or more additional contact elements in electrical contact with and optionally disposed within each of the one or more electrically conducting contact rings 130, 175. These one or more additional contact elements are configured to provide electrical communication between one or more electrically conducting contact rings 130, 175 and a lead contact received within the lead aperture 165. In many embodiments, these contact elements are electrically conductive and resilient to provide an interference fit between the electrically conducting contact ring 130, 175 and lead contact received within the lead aperture 165.

Examples of contact elements include, but are not limited to, spring elements. In many embodiments, the contact element includes an annular helical coil 150 (i.e., continuous coil spring 150) is disposed adjacent an inner surface of the electrically conducting contact ring 130. The helical annular coil 150 can be formed of any useful electrically conductive material such as, for example, a metal like gold, silver, platinum, titanium and the like. When a lead in inserted into the lead aperture 165, the lead and lead contact(s) can deflect the annular helical coil 150 and form an electrical contact between the lead contact and the electrically conducting contact ring 130. The continuous coil spring 150 provides a electrical pressure contact and mechanical engagement with a lead contact and the adjacent electrically conducting contact ring 130 and 175.

A seal element 178 may also be included in 105 aperture to provide electrical isolation between contacts 150 and/or between lead contacts when a lead is inserted into the lead aperture 165. The seal element 178 can be any useful electrically insulating material such as elastomeric material or polymeric material. The seal element 178 can be an annular element that is disposed between the electrically conducting contact rings 130, 175.

A mounting flange 160 can be fixed to the lead connector 105 adjacent the open end 166. The mounting flange 160 can be brazed or welded to the chassis element 110. In many embodiments, the mounting flange 160 can be brazed or welded to the chassis element 110 first major surface 112 or opposing second major surface 114. A retention member (not shown) such as for example, a set screw, can be disposed on the lead connector 105 adjacent to the open end 166 and can assist in mechanical retention of the lead disposed within the lead aperture 165.

The lead connector 105 can be formed by any useful method. In many embodiments, the lead connector 105 is formed by assembling two or more lead connector subassemblies 106. FIG. 5 is an exploded perspective cut-away view of the illustrative subassembly 106 shown in FIG. 4. FIG. 6 is a perspective cut-away view of another illustrative subassembly 107 that includes an optional ceramic spacer ring 141 separating the electrically conducting contact rings 130 and 175. Each lead connector subassembly 106 or 107 can be arranged in axial alignment and bonded utilizing a metal to metal bonding technique such as, laser welding, for example, to form the lead connector 105.

Each lead connector subassembly 106 includes the electrically insulating ring 140 fixed between the electrically conducting contact ring 130 and an attachment ring or electrically conducting spacer ring 175. Thus, the electrically conducting spacer ring 175 is affixed to a first side of the electrically insulating ring 140 and the electrically conducting contact ring 130 is affixed to a second opposing side of the electrically insulating ring 140. The lead connector subassembly 106 includes the electrically insulating ring 140 bonding the electrically conducting contact ring 130 to the electrically conducting spacer ring 175. The electrically insulating ring 140 is integral to the hermetic seal between the between the sealed housing interior/lead connector outer surface 70 and the lead aperture 165.

The electrically conducting spacer ring 175 can be formed of any useful electrically conductive material. In many embodiments, the electrically conducting spacer ring 175 is formed of a metallic material such as, for example, titanium, stainless steel, MP35N, niobium, tantalum, platinum, and alloys or combinations thereof. In some embodiments, the one electrically conducting spacer ring 175 is formed of a metallic material such as, for example, titanium.

In some embodiments, as illustrated in FIG. 5 and FIG. 7, the electrically conducting contact ring 130 and electrically conducting spacer ring 175 form an overlapping joint. The electrically insulating material 140 at least partially filling the overlapping joint space separating the electrically conducting contact ring 130 and electrically conducting spacer ring 175. The overlapping joint can improve the structural integrity of the electrically insulating material 140 bond.

FIG. 9 is a schematic perspective view of another implantable active medical device 200 having two elongate lead connectors 105 (described above) with rigid sleeves 202 disposed about the elongate lead connectors 105. The rigid sleeve 202 is fixed to the chassis plate 110 and disposed about the elongate lead connector 105. In many embodiments the rigid sleeve 202 is welded or brazed to the first major surface 112 of the chassis plate 110. A portion of one of the rigid sleeves 202 is shown as cut-away for ease of illustration of the enclosed elongate lead connector 105.

The rigid sleeve 202 can be formed of any useful structurally rigid material. In many embodiments the rigid sleeve 202 is a metal sleeve that is electrically isolated from the contacts in the elongate lead connector 105. The rigid sleeve 202 has a proximal end 201 fixed to the chassis plate 110 and an opposing distal end 203. In many embodiments, the distal end 203 includes a mounting surface 204 for fixing the circuit board 50 to the rigid sleeve 202. As illustrated in FIG. 9, the mounting surface 204 is parallel to the circuit board 50. In many embodiments the circuit board 50 is fixed to the mounting surface 204 of the rigid sleeve 202 via a screw 206.

The illustrated lead connector 105 is an elongate member extending between a lead aperture 165 first open end and an end cap, and having an inner surface defining an open lumen lead aperture 165. The elongate lead connector 105 is further described with regard to FIGS. 4-8 above.

Electronics 50 are fixed to the first major surface 112 and extending orthogonally away from the first major surface 112, as described above. As illustrated in FIG. 9, the electronics or circuit board 50 is fixed to and between elongate lead connectors 105 and chassis plate 110. This configuration results in a stable assembly where the displacement of the parts relative to each other has been substantially minimized.

A hermetic housing (not shown) defines a sealed housing cavity. The hermetic housing is fixed to the first major surface 112, as illustrated in FIG. 3. The elongate lead connector 105 and the circuit board 50 are disposed within the sealed housing cavity. The hermetic housing 70 is a metallic shell. In many embodiments, a power source 60 is fixed to the chassis 110 second major surface 114, as described above, although it can be fixed to any surface of chassis 110. The power source 60 can be fixed to the first major surface 112 and contained entirely within the hermetic enclosure defined by the hermetic housing 70. The power source 60 can be electrically connected to the circuit board 50 through the chassis plate 110 via electrical connectors 56. The power source 60 can be any useful battery or inductive coil.

In many embodiments the elongate lead connectors 105 are fixed at the proximal end 201 to the first major surface 112 of the chassis plate 110 and are fixed at the opposing distal end 204 to the circuit board 50. In these embodiments, the elongate lead connectors 105 is in cantilever arrangement within the hermetic enclosure of the hermetic housing 70.

In some embodiments the circuit board and/or the power source can be entirely or only fixed to the rigid sleeve and/or elongate lead connectors 105. Then, the elongate lead connectors 105 fixed to the chassis plate 110 provides a rigid structure that any combination of other components can be fixated to. In other embodiments the circuit board and/or the power source can be fixed to the rigid sleeve and/or elongate lead connectors 105 and also fixed to the chassis plate 110.

Thus, embodiments of the IMPLANTABLE DEVICE WITH CHASSIS ELEMENT are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. An implantable active medical device comprising:
 a chassis plate having a first major surface and an opposing second major surface;
 an elongate lead connector configured to receive a lead, wherein the elongate lead connector is fixed to the first major surface and extends orthogonally away from the first major surface;
 a circuit board having a length, a width, and a thickness, the length being greater than the width and the thickness, the circuit board fixed to and extending orthogonally away from the first major surface in the direction of the length; and
 a hermetic housing defining a sealed housing cavity, the hermetic housing fixed to the first major surface and the elongate lead connector and the circuit board are disposed within the sealed housing cavity.

2. The implantable active medical device according to claim 1, wherein the elongate lead connector comprises a closed end, an open end hermetically joined to the chassis plate, an outer surface at least partially defining the sealed housing interior, and an inner surface defining a lead aperture.

3. The implantable active medical device according to claim 2, wherein the elongate lead connector comprises two or more electrically conducting contact rings spaced apart by a ring of electrically insulating material, the two or more electrically conducting contact rings in electrical communication with the circuit board, and the ring of electrically insulating material providing a hermetic seal between the lead connector outer surface and the lead connector inner surface.

4. The implantable active medical device according to claim 1, further comprising a power source fixed to the chassis plate.

5. The implantable active medical device according to claim 4, wherein the power source is electrically connected to the circuit board through the chassis plate.

6. The implantable active medical device according to claim 1, wherein the elongate lead connector is disposed through the chassis plate.

7. The implantable active medical device according to claim 1, wherein the elongate lead connector is fixed mechanically and electrically to the circuit board.

8. The implantable active medical device according to claim 1, wherein the elongate lead connector is coextensive with the circuit board.

9. An implantable active medical device according to claim 1, further comprising a second elongate lead connector fixed to the first major surface and extending orthogonally away from the first major surface.

10. An implantable active medical device according to claim 1, further comprising a rigid sleeve fixed to the chassis plate and disposed about the elongate lead connector.

11. An implantable active medical device according to claim 10, wherein the rigid sleeve has a proximal end fixed to the chassis plate and an opposing distal end, the distal end including a mounting surface for fixing the circuit board to the rigid sleeve.

12. An implantable active medical device according to claim 11, wherein the mounting surface is parallel to the circuit board.

13. An implantable active medical device comprising:
a chassis plate having a first major surface and an opposing second major surface;
a first elongate lead connector configured to receive a lead, wherein the first elongate lead connector is fixed to the first major surface and extends orthogonally away from the first major surface;
a second elongate lead connector configured to receive a lead, wherein the second elongate lead connector is fixed to the first major surface and extends orthogonally away from the first major surface;
a circuit board having a length, a width, and a thickness, the length being greater than the width and the thickness, the circuit board fixed to and extending orthogonally away from the first major surface in the direction of the length, the circuit board being disposed between the first elongate lead connector and the second elongate lead connector; and
a hermetic housing defining a sealed housing cavity, the hermetic housing fixed to the first major surface and the first elongate lead connector, second elongate lead connector and the circuit board are disposed within the sealed housing cavity.

14. The implantable active medical device according to claim 13, wherein the first elongate lead connector comprises a first closed end, a first open end hermetically joined to the chassis plate, a first outer surface at least partially defining the sealed housing interior, and a first inner surface defining a first lead aperture.

15. The implantable active medical device according to claim 14, wherein the first elongate lead connector comprises two or more electrically conducting contact rings spaced apart by a ring of electrically insulating material, the two or more electrically conducting contact rings in electrical communication with the circuit board, and the ring of electrically insulating material providing a hermetic seal between the first lead connector outer surface and the first lead connector inner surface.

16. The implantable active medical device according to claim 13, further comprising a power source fixed to the second major surface.

17. The implantable active medical device according to claim 16, wherein the power source is electrically connected to the circuit board through the chassis plate.

18. The implantable active medical device according to claim 13, wherein the first elongate lead connector is disposed through the chassis plate and the second elongate lead connector is disposed through the chassis plate.

19. The implantable active medical device according to claim 13, wherein the first elongate lead connector is fixed mechanically and electrically to the circuit board and the second elongate lead connector is fixed mechanically and electrically to the circuit board.

20. The implantable active medical device according to claim 13, wherein the first elongate lead connector is coextensive with the circuit board and the second elongate lead connector is coextensive with the circuit board.

21. The implantable active medical device according to claim 20, wherein the circuit board separates the first elongate lead connector from the second elongate lead connector.

22. An implantable active medical device according to claim 13, further comprising a rigid sleeve fixed to the chassis plate and disposed about the first elongate lead connector.

23. An implantable active medical device according to claim 22, wherein the rigid sleeve has a proximal end fixed to the chassis plate and an opposing distal end, the distal end including a mounting surface for fixing the circuit board to the rigid sleeve.

24. An implantable active medical device according to claim 23, wherein the mounting surface is parallel to the circuit board.

* * * * *